United States Patent
Lin et al.

(10) Patent No.: US 9,821,147 B2
(45) Date of Patent: Nov. 21, 2017

(54) MULTILAYER BALLOON FOR A CATHETER

(71) Applicant: ABBOTT CARDIOVASCULAR SYSTEMS INC., Santa Clara, CA (US)

(72) Inventors: Tung-Liang Lin, Temecula, CA (US); Jeong S. Lee, Diamond Bar, CA (US); Roseminda White, Wildomar, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 314 days.

(21) Appl. No.: 14/820,664

(22) Filed: Aug. 7, 2015

(65) Prior Publication Data
US 2015/0343180 A1     Dec. 3, 2015

Related U.S. Application Data

(63) Continuation of application No. 13/680,299, filed on Nov. 19, 2012, now Pat. No. 9,132,259.

(51) Int. Cl.
*A61M 25/10* (2013.01)
*B29C 49/22* (2006.01)
(Continued)

(52) U.S. Cl.
CPC ............ *A61M 25/10* (2013.01); *A61L 29/04* (2013.01); *A61L 29/126* (2013.01);
(Continued)

(58) Field of Classification Search
CPC .......... A61M 2025/1075; A61M 25/10; A61M 25/1029; A61M 25/104;
(Continued)

(56) References Cited

U.S. PATENT DOCUMENTS

| 4,952,357 A | 8/1990 | Euteneuer |
| 5,112,304 A | 5/1992 | Barlow et al. |

(Continued)

FOREIGN PATENT DOCUMENTS

| EP | 0420488 | 3/1991 |
| EP | 0485903 | 10/1996 |

(Continued)

OTHER PUBLICATIONS

U.S. Appl. No. 12/881,733, dated Oct. 11, 2013 Applicant-Initiated Interview Summary.

(Continued)

*Primary Examiner* — Quynh-Nhu H Vu
(74) *Attorney, Agent, or Firm* — Baker Botts L.L.P.

(57) ABSTRACT

Balloon catheter comprises an elongate catheter shaft having a proximal section, a distal section, and an inflation lumen defined therein and a multilayer balloon on the distal section of the shaft comprising a first layer made of a first polymer material having a first Shore durometer hardness, a second layer made of a second polymer material having a second Shore durometer hardness greater than the first Shore durometer hardness, wherein the second layer is an inner layer relative to the first layer, and a third layer made of a third polymer material having a third Shore durometer hardness less the first Shore durometer hardness, wherein the third layer is an inner layer relative to the second layer. Method of making a balloon catheter is also provided.

35 Claims, 9 Drawing Sheets

(51) Int. Cl.
*A61L 29/04* (2006.01)
*A61L 29/12* (2006.01)
*B29K 77/00* (2006.01)
*B29L 31/00* (2006.01)
*A61F 2/958* (2013.01)

(52) U.S. Cl.
CPC ...... *A61M 25/104* (2013.01); *A61M 25/1029* (2013.01); *B29C 49/22* (2013.01); *A61F 2/958* (2013.01); *A61M 2025/1075* (2013.01); *A61M 2025/1084* (2013.01); *B29K 2077/00* (2013.01); *B29K 2995/007* (2013.01); *B29L 2031/7543* (2013.01)

(58) Field of Classification Search
CPC ...... A61M 2025/1084; A61M 25/0009; A61M 25/1027; B29C 49/22; B29C 49/04; B29C 67/0014; B29K 2077/00; B29K 2995/007; B29L 2031/7543
See application file for complete search history.

(56) References Cited

U.S. PATENT DOCUMENTS

| | | |
|---|---|---|
| 5,195,969 A | 3/1993 | Wang et al. |
| 5,207,700 A | 5/1993 | Euteneuer |
| 5,270,086 A | 12/1993 | Hamlin |
| 5,290,306 A | 3/1994 | Trotta et al. |
| 5,358,486 A | 10/1994 | Saab |
| 5,447,497 A | 9/1995 | Sogard et al. |
| 5,478,320 A | 12/1995 | Trotta |
| 5,499,980 A | 3/1996 | Euteneuer |
| 5,512,051 A | 4/1996 | Wang et al. |
| 5,556,383 A | 9/1996 | Wang et al. |
| 5,587,125 A | 12/1996 | Roychowdhury |
| 5,613,979 A | 3/1997 | Trotta et al. |
| 5,620,649 A | 4/1997 | Trotta |
| 5,647,848 A | 7/1997 | Jorgensen |
| 5,679,817 A | 10/1997 | Sakai et al. |
| 5,755,690 A | 5/1998 | Saab |
| 5,769,817 A | 6/1998 | Burgmeier |
| 5,797,887 A | 8/1998 | Rosen et al. |
| 5,807,327 A | 9/1998 | Green et al. |
| 5,833,657 A | 11/1998 | Reinhardt et al. |
| 5,879,369 A | 3/1999 | Ishida |
| 5,908,406 A | 6/1999 | Ostapchenko et al. |
| 6,004,289 A | 12/1999 | Saab |
| 6,004,339 A | 12/1999 | Wijay |
| 6,024,722 A | 2/2000 | Rau et al. |
| 6,059,751 A | 5/2000 | Ostapchenko et al. |
| 6,086,556 A | 7/2000 | Hamilton et al. |
| 6,124,007 A | 9/2000 | Wang et al. |
| 6,132,824 A | 10/2000 | Hamlin |
| 6,136,258 A | 10/2000 | Wang et al. |
| 6,146,356 A | 11/2000 | Wang et al. |
| 6,171,278 B1 | 1/2001 | Wang et al. |
| 6,242,063 B1 | 6/2001 | Ferrera et al. |
| 6,328,925 B1 | 12/2001 | Wang et al. |
| 6,358,227 B1 | 3/2002 | Ferrera et al. |
| 6,416,494 B1 | 7/2002 | Wilkins |
| 6,495,090 B1 | 12/2002 | Wilkins |
| 6,500,148 B1 | 12/2002 | Pinchuk et al. |
| 6,585,688 B2 | 7/2003 | Ferrera et al. |
| 6,620,127 B2 | 9/2003 | Lee et al. |
| 6,620,128 B1 | 9/2003 | Simhambhatla |
| 6,645,422 B2 | 11/2003 | Jung et al. |
| 6,673,302 B2 | 1/2004 | Wang et al. |
| 6,695,809 B1 | 2/2004 | Lee |
| 6,756,094 B1 | 6/2004 | Wang et al. |
| 6,796,960 B2 | 9/2004 | Cioanta et al. |
| 6,835,189 B2 | 12/2004 | Musbach et al. |
| 6,866,650 B2 | 3/2005 | Stevens et al. |
| 6,875,197 B1* | 4/2005 | Simhambhatla ........ A61L 29/06 604/103.06 |
| 6,896,842 B1 | 5/2005 | Hamilton et al. |
| 6,911,038 B2 | 6/2005 | Mertens et al. |
| 6,946,092 B1 | 9/2005 | Bertolino et al. |
| 6,949,112 B1 | 9/2005 | Sridharan et al. |
| 6,951,675 B2 | 10/2005 | Chin et al. |
| 7,026,026 B2 | 4/2006 | Ferrera et al. |
| 7,029,732 B2 | 4/2006 | Wang et al. |
| 7,074,206 B2 | 7/2006 | Lee et al. |
| 7,112,357 B2 | 9/2006 | Miller et al. |
| 7,147,817 B1 | 12/2006 | Lim et al. |
| 7,195,638 B1 | 3/2007 | Sridharan |
| 7,335,185 B2 | 2/2008 | Tang et al. |
| 7,781,038 B2 | 8/2010 | Hamilton et al. |
| 7,815,628 B2 | 10/2010 | Devens, Jr. |
| 7,828,766 B2* | 11/2010 | Durcan ................ A61F 2/958 604/103.06 |
| 7,906,066 B2 | 3/2011 | Wilson et al. |
| 7,942,847 B2 | 5/2011 | Stupecky et al. |
| 8,388,575 B2 | 3/2013 | Durcan et al. |
| 8,394,055 B2 | 3/2013 | Durcan et al. |
| 8,535,596 B2 | 9/2013 | Durcan |
| 8,703,260 B2 | 4/2014 | Simpson |
| 9,095,689 B2 | 8/2015 | Durcan |
| 9,132,259 B2* | 9/2015 | Lin ................ A61M 25/1029 |
| 2002/0018866 A1* | 2/2002 | Lee ................ A61L 29/06 428/36.8 |
| 2002/0087165 A1 | 7/2002 | Lee et al. |
| 2002/0118866 A1 | 8/2002 | Breeuwer et al. |
| 2002/0165523 A1 | 11/2002 | Chin et al. |
| 2002/0171180 A1 | 11/2002 | Simhambhatla |
| 2004/0096606 A1* | 5/2004 | Lee ................ A61L 29/049 428/35.2 |
| 2004/0170782 A1 | 9/2004 | Wang et al. |
| 2004/0173935 A1 | 9/2004 | Lim et al. |
| 2004/0191443 A1 | 9/2004 | Hamlin |
| 2005/0043679 A1 | 2/2005 | Devens et al. |
| 2005/0124976 A1 | 6/2005 | Devens, Jr. et al. |
| 2005/0186370 A1 | 8/2005 | Hamilton et al. |
| 2005/0228429 A1 | 10/2005 | Burgmeier et al. |
| 2005/0238833 A1 | 10/2005 | Wang et al. |
| 2005/0277878 A1 | 12/2005 | Lee |
| 2006/0165926 A1 | 7/2006 | Weber |
| 2007/0060863 A1 | 3/2007 | Goeken et al. |
| 2007/0142771 A1* | 6/2007 | Durcan ................ A61F 2/958 604/103.06 |
| 2007/0142772 A1 | 6/2007 | Deshmuhk et al. |
| 2007/0167973 A1 | 7/2007 | Stupecky et al. |
| 2007/0250101 A1 | 10/2007 | Horn et al. |
| 2008/0045928 A1 | 2/2008 | Simpson et al. |
| 2008/0065188 A1 | 3/2008 | Pallazza |
| 2009/0156998 A1 | 6/2009 | Arana et al. |
| 2010/0010470 A1 | 1/2010 | Bates |
| 2011/0022150 A1 | 1/2011 | Durcan |
| 2012/0065718 A1 | 3/2012 | Simpson et al. |
| 2012/0145317 A1 | 6/2012 | Durcan et al. |
| 2012/0203324 A1 | 8/2012 | Durcan |
| 2013/0172817 A1 | 7/2013 | Durcan et al. |
| 2014/0142505 A1 | 5/2014 | Lin et al. |
| 2014/0190630 A1 | 7/2014 | Simpson et al. |

FOREIGN PATENT DOCUMENTS

| | | |
|---|---|---|
| EP | 0611576 | 1/1997 |
| EP | 0 768 097 | 4/1997 |
| EP | 0592885 | 7/2009 |
| JP | H05-305146 | 11/1993 |
| JP | H06-507101 | 8/1994 |
| JP | 2001/1029450 | 2/2001 |
| JP | 2005-167638 | 6/2005 |
| JP | 2007/000157 | 1/2007 |
| WO | WO 92/08512 | 5/1992 |
| WO | WO 95/18647 | 7/1995 |
| WO | WO 01/51115 | 7/2001 |
| WO | WO 02/056930 | 7/2002 |
| WO | WO 2005/021083 | 3/2005 |

(56) References Cited

FOREIGN PATENT DOCUMENTS

| | | |
|---|---|---|
| WO | WO 2005/065735 | 7/2005 |
| WO | WO2006/126311 | 11/2006 |

OTHER PUBLICATIONS

U.S. Appl. No. 13/680,299, dated Nov. 10, 2014 Response to Restriction Requirement.
U.S. Appl. No. 13/680,299, dated Sep. 8, 2014 Restriction Requirement.
International Search Report dated Jul. 23, 2014 in PCT/US2013/070540.
U.S. Appl. No. 14/443,805, dated May 19, 2015.
U.S. Appl. No. 14/748,376, dated Jun. 24, 2015.
U.S. Appl. No. 11/313,041, dated Oct. 4, 2010 Issue Fee payment.
U.S. Appl. No. 11/313,041, dated Jul. 2, 2010 Notice of Allowance.
U.S. Appl. No. 11/313,041, dated Jun. 4, 2010 Request for Continued Examination (RCE).
U.S. Appl. No. 11/313,041, dated Apr. 6, 2010 Notice of Allowance.
U.S. Appl. No. 11/313,041, dated Mar. 1, 2010 Amendment and Request for Continued Examination (RCE).
U.S. Appl. No. 11/313,041, dated Oct. 27, 2009 Final Office Action.
U.S. Appl. No. 11/313,041, dated Jun. 22, 2009 Response to Non-Final Office Action.
U.S. Appl. No. 11/313,041, dated Apr. 17, 2009 Examiner Interview Summary.
U.S. Appl. No. 11/313,041, dated Jan. 22, 2009 Non-Final Office Action.
U.S. Appl. No. 11/313,041, dated Dec. 8, 2008 Amendment and Request for Continued Examination (RCE).
U.S. Appl. No. 11/313,041, dated Sep. 16, 2008 Final Office Action.
U.S. Appl. No. 11/313,041, dated May 12, 2008 Response to Non-Final Office Action.
U.S. Appl. No. 11/313,041, dated Feb. 21, 2008 Non-Final Office Action.
U.S. Appl. No. 12/881,733, dated Mar. 4, 2014 Issue Fee Payment.
U.S. Appl. No. 12/881,733, dated Dec. 4, 2013 Notice of Allowance.
U.S. Appl. No. 12/881,733, dated Oct. 30, 2013 Response to Non-Final Office Action.
U.S. Appl. No. 12/881,733, dated Oct. 17, 2013 Applicant-Initiated Interview Summary.
U.S. Appl. No. 12/881,733, dated Sep. 24, 2013 Applicant-Initiated Interview Summary.
U.S. Appl. No. 12/881,733, dated May 30, 2013 Non-Final Office Action.
U.S. Appl. No. 12/881,733, dated Mar. 12, 2013 Response to Restriction Requirement.
U.S. Appl. No. 12/881,733, dated Feb. 12, 2013 Restriction Requirement.
U.S. Appl. No. 12/897,202, dated Feb. 7, 2013 Issue Fee payment.
U.S. Appl. No. 12/897,202, dated Nov. 7, 2012 Notice of Allowance.
U.S. Appl. No. 13/397,140, dated Aug. 16, 2013 Issue Fee Payment.
U.S. Appl. No. 13/397,140, dated May 17, 2013 Notice of Allowance.
U.S. Appl. No. 13/397,140, dated Feb. 26, 2013 Response to Non-Final Office Action.
U.S. Appl. No. 13/397,140, dated Oct. 26, 2012 Non-Final Office Action.
U.S. Appl. No. 13/447,635, dated Feb. 5, 2013 Issue Fee payment.
U.S. Appl. No. 13/447,635, dated Nov. 5, 2012 Notice of Allowance.
U.S. Appl. No. 13/775,724, dated Nov. 20, 2014 Non-Final Office Action.
U.S. Appl. No. 13/775,724, dated Feb. 20, 2015 Response to Non-Final Office Action.
U.S. Appl. No. 13/775,724, dated Feb. 26, 2015 Applicant-Initiated Interview Summary.
U.S. Appl. No. 13/775,724, dated Mar. 24, 2015 Notice of Allowance.
U.S. Appl. No. 13/775,724, dated Jun. 24, 2015 Issue Fee Payment.
U.S. Appl. No. 13/680,299, dated Nov. 26, 2014 Non-Final Office Action.
U.S. Appl. No. 13/680,299, dated Feb. 24, 2015 Response to Non-Final Office Action.
U.S. Appl. No. 13/680,299, dated May 8, 2015 Notice of Allowance.
U.S. Appl. No. 13/680,299, dated Aug. 7, 2015 Issue Fee Payment.
U.S. Appl. No. 13/775,752, dated Aug. 5, 2015 Notice of Allowance.
U.S. Appl. No. 14/204,885, dated Oct. 6, 2015 Non-Final Office Action.
Material Testing Analysis & Characterization of Traytuf 7357 (5 pages) 2007 (month and date are not available).
Nylon Plastics Handbook, Melvin I. Kohan 1995, pp. 298-302 (month and date are not available).
Thesis for the Degree of Master of Science by Samantha Garramone, (65 pages) 2001 (month and date are not available).
Concise Encyclopedia of Polymer Science and Engineering, p. 759, 815, 1990 (month and date are not available).
("Hytrel" data sheet) including Hytrel TPC-ET, (94 pages), date not available.
DuPont Product Information, "Hytrel polyester elastomer", Nov. 1993 (date is not available).
DuPont Product Information, Injection Molding Guide, "Hytrel polyester elastomer", Oct. 1996 (date is not available).
DuPont Engineering Polymers, "From concept to commercialisation," (40 pages) Sep. 1996 (date is not available).
DuPont Product and Properties Guide, "Hytrel polyester elastomer" Nov. 1999 (date is not available).
Data Sheets of Hytrel grades (2 pages), date not available.
Table "Hytrel grades available before Oct. 1996" (date is not available).
Mat Web Information for Plexar (25 pages) Accessed Oct. 20, 2008.
"Synthesis and characterization of hyperbranched polyglycerol hydrogels," Oudshoorn et al., Biomaterials, 27:5471-5479, Jul. 2006 (date is not available).
Ahearne, et al., "Mechanical characterisation of hydrogels for tissue engineering applications," Topics in Tissue Engineering, 4 (Chapter 12): 3-16, 2008 (month and date are not available).
Technical data sheet "TRAYTUF® 7357 Polyester Resin", date not available.
Technical data sheet "SELAR PT 4368" Oct. 31, 1990.
Affidavit of Dr. John Chen regarding the measurements for Traytuf 7357 mentioned in Material Testing analysis & Characterization of Traytuf 7357. 2009 (month and date are not available).
"Comparison of ARNITEL EL 740 With HYTREL 7246", retrieved from co-pending U.S. Appl. No. 11/313,041, filed Apr. 1, 2013.
"CLEARTUF 8006", Shell Chemical Company. date not available.
Extract from Wikipedia, "Polyimide" (2 sheets) 2009 (month and date are not available).
Data sheet Aurum PL450C (2 sheets), received Oct. 19, 2009.

* cited by examiner

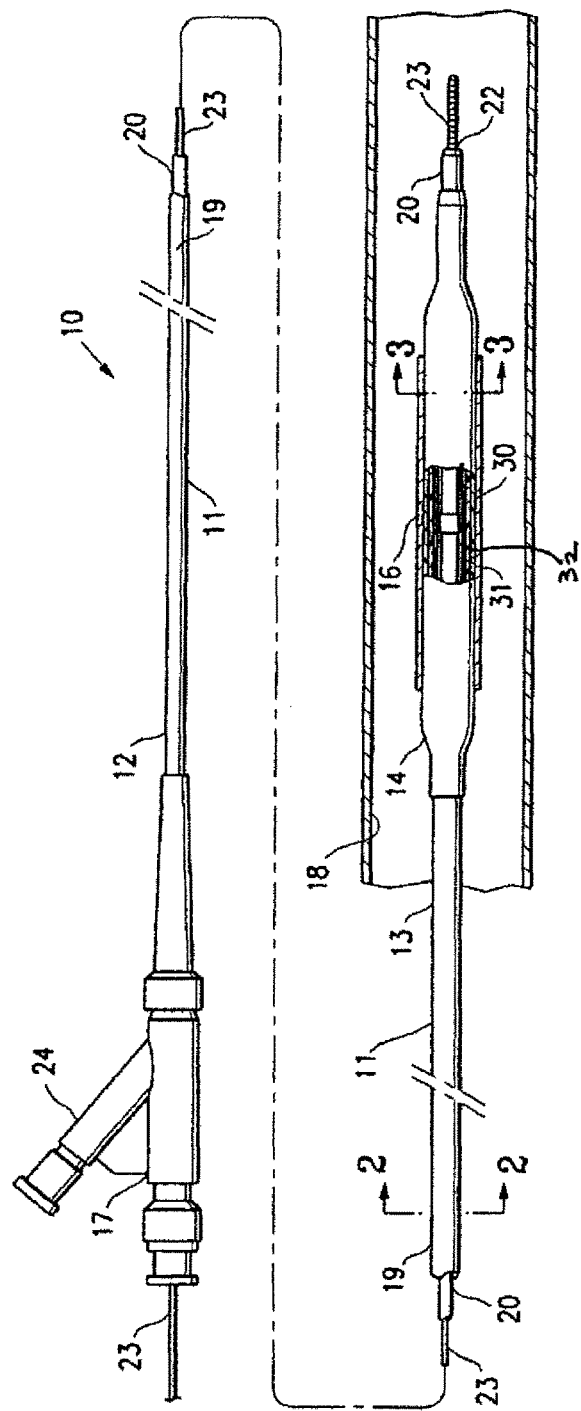
FIG. 1
FIG. 2
FIG. 3

| Sample | Materials (Pebax unless otherwise specified) & Thickness (mil) | Extrusion ID / OD (inches) | Mold ID (inches) & BUR | Blow Process | Balloon size/ OD | Average DWT (mil) | Min DWT (mil) | Max DWT (mil) | Compliance Slope (12-20) atm | Rupture Average (atm) | Calculated RBP (atm) | Axial Growth 2 to Nominal | Axial Growth Nominal to RBP | Hoop Strength (psi) | Fatigue (20atm / 20 cycles) |
|---|---|---|---|---|---|---|---|---|---|---|---|---|---|---|---|
| Control | 72D single layer (9.3) | 0.018 / 0.0365 | 0.116 / 6.44 | Single | 3x18 / 0.117 | 1.52 | 1.47 | 1.57 | 0.020 (10-20 atm) | 28 | 24.4 | 4.22% | 3.75% | 31,661 | Pass (18 atm) |
| 1 | 63D/72D/70D (2.0/6.25/2.0) | 0.0150 / 0.0355 | 0.116 / 7.75 | Single | 3x18 / 0.118 | 1.37 | 1.31 | 1.43 | 0.019 (10-20 atm) | 26.85 | 22.02 | 4.54% | 2.78% | 33,505 | Pass (18 atm) |
| 2 | 63D/72D/70D (2.0/6.25/2.0) | 0.0150 / 0.0355 | 0.116 / 7.75 | Double | 3x25 / 0.116 | 1.62 | 1.57 | 1.67 | 0.014(10-20 atm) | 29.31 | 24.74 | 3.21% | 5.25% | 30,861 | Pass |
| 3 | 63D/Nylon/70D (3.1/4.0/3.1) | 0.015 / 0.0355 | 0.116 / 7.75 | Double | 3x28 / 0.116 | 1.6 | 1.55 | 1.65 | 0.0129 | 31.9 | 26.48 | 3.76% | 5.00% | 34,002 | Pass |
| 4 | 63D/Nylon/70D (3.5/4.0/3.5) | 0.0168 / 0.0388 | 0.125 / 7.50 | Single | 3.25x28 / 0.126 | 1.64 | 1.59 | 1.7 | 0.0172 | 30.1 | 25.22 | 4.45% | 3.63% | 33,983 | Pass |
| 5 | 63D/Nylon/70D (3.05/5.0/3.0) | 0.0168 / 0.0388 | 0.125 / 7.50 | Single | 3.25x28 / 0.126 | 1.62 | 1.59 | 1.65 | 0.0163 | 32.3 | 27.4 | 4.68% | 3.21% | 36,944 | Pass |
| 6 | 63D/Nylon/70D (4.5/5.0/4.5) | 0.024 / 0.052 | 0.201 / 8.17 | Double | 5x20 / 0.196 | 2.13 | 2.07 | 2.2 | 0.0154 | 26.6 | 23.09 | N/A | N/A | 36,006 | Pass |

Figure 6

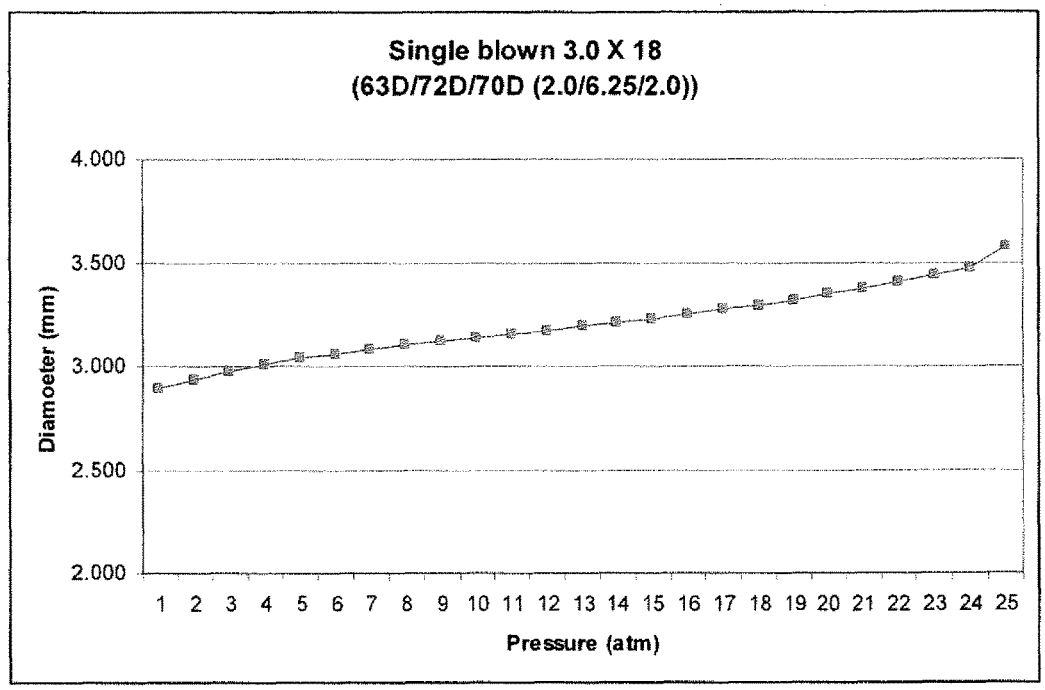
Figure 7: Sample 1

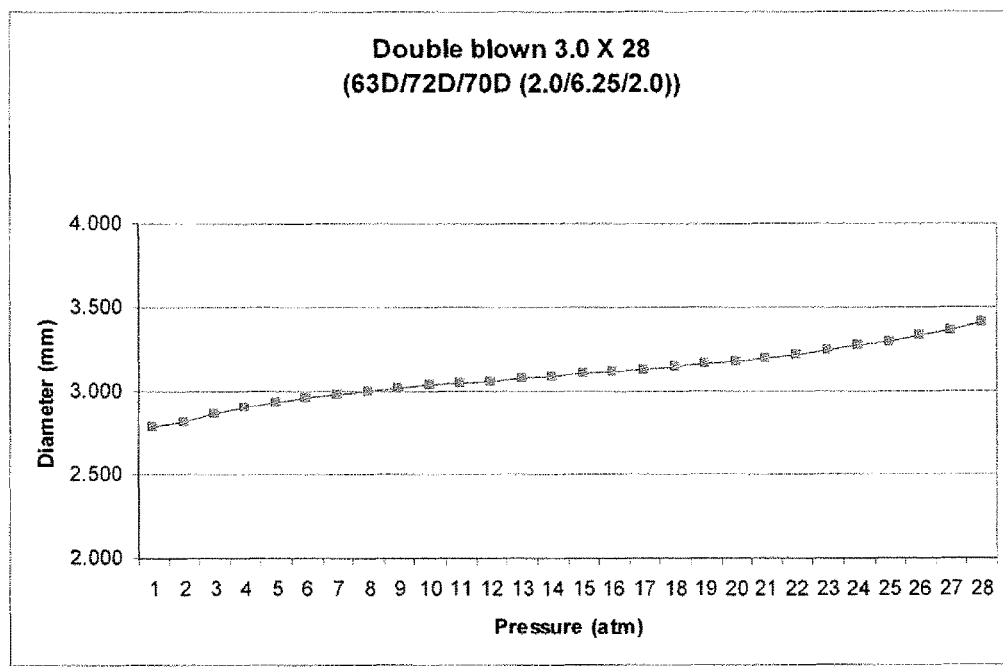
Figure 8: Sample 2

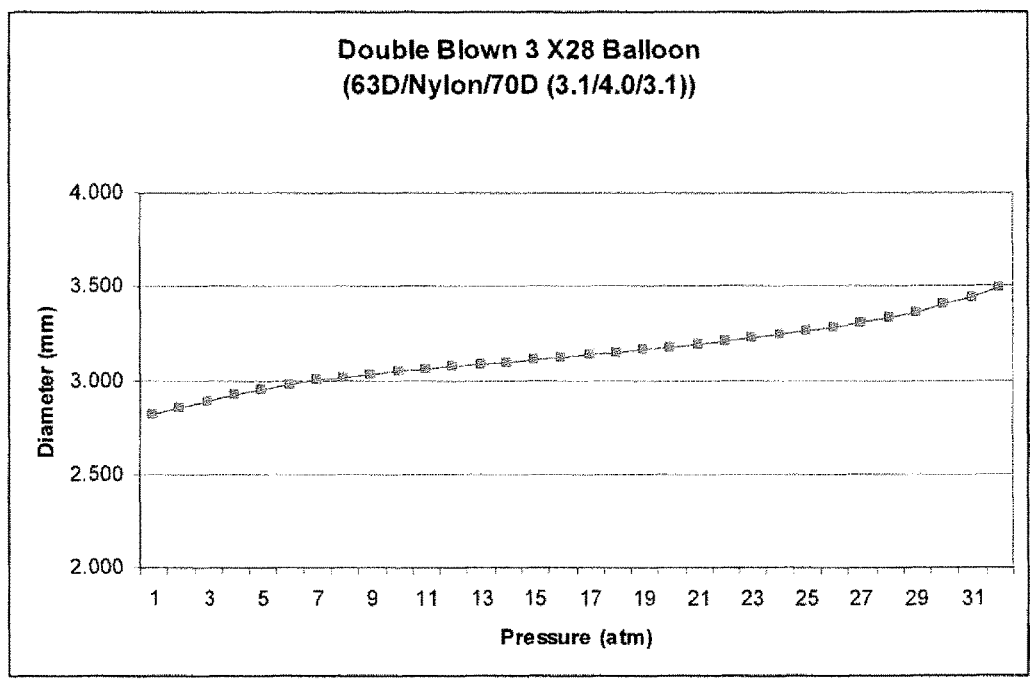
Figure 9: Sample 3

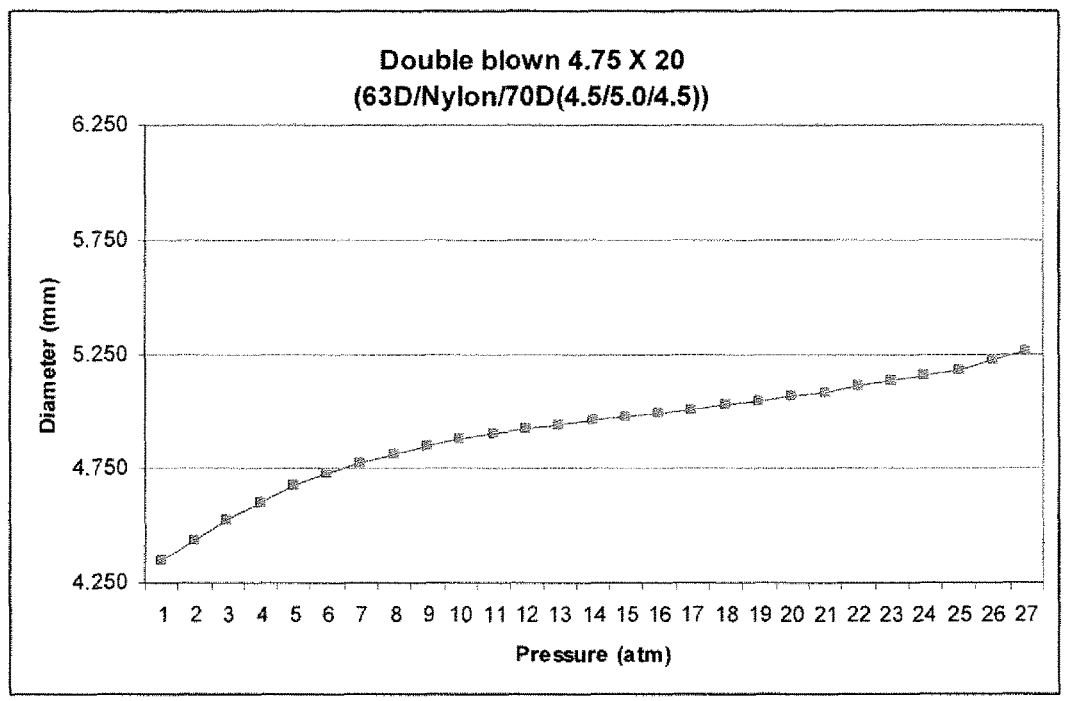
Figure 10: Sample 6

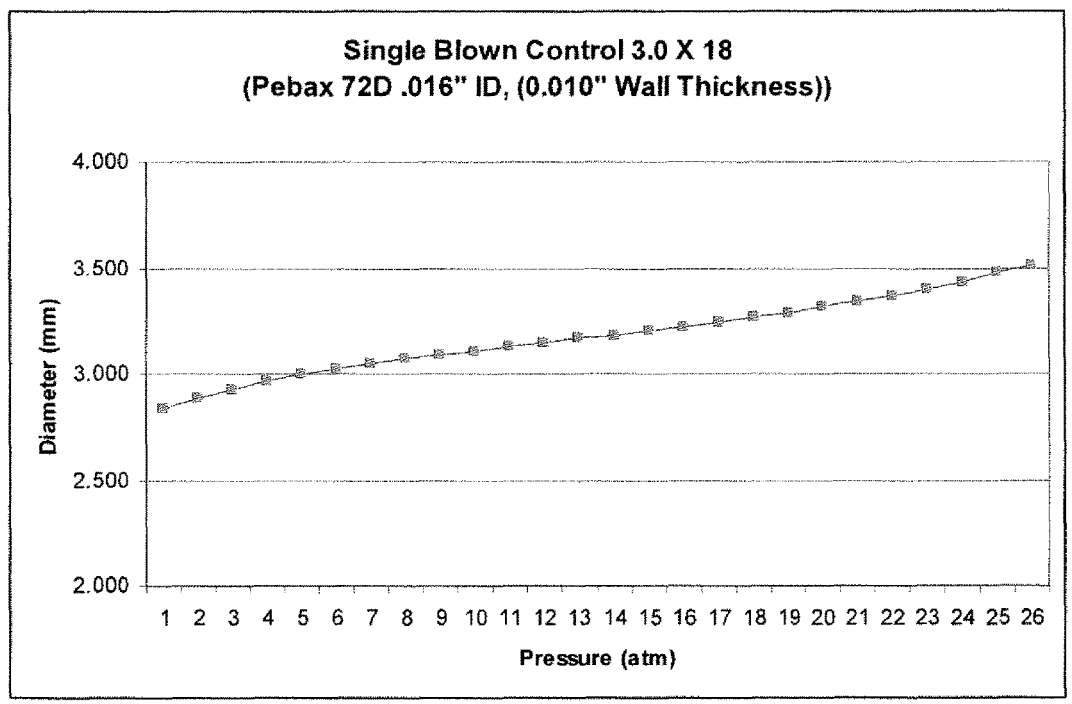
Figure 11: Control

MULTILAYER BALLOON FOR A CATHETER

CROSS-REFERENCE TO RELATED APPLICATIONS

This application is a continuation of U.S. patent application Ser. No. 13/680,299 filed Nov. 19, 2012, which is incorporated by reference herein in its entirety

BACKGROUND OF THE DISCLOSED SUBJECT MATTER

Field of the Disclosed Subject Matter

The disclosed subject matter is related to the field of intravascular medical devices. More particularly, the presently disclosed subject matter relates to a multilayer balloon for a catheter.

Description of Related Subject Matter

Balloon catheters are used for a variety of treatments and techniques for intralumenal indications throughout the body, including the cardiovascular and peripheral systems. One such method is known as a percutaneous transluminal coronary angioplasty (PTCA) procedure. For purpose of example, in PTCA procedures, a guiding catheter is advanced until the distal tip of the guiding catheter is seated in the ostium of a desired coronary artery. A guidewire is then advanced out of the distal end of the guiding catheter into the patient's coronary artery until the distal end of the guidewire crosses a lesion to be dilated. A dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with liquid or suitable inflation medium one or more times to a predetermined size at relatively high pressures (e.g. greater than 8 atmospheres) to compress the stenosis against the arterial wall and thus open the passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents can also be used to repair vessels having an intimal flap or dissection or to generally strengthen a weakened section of a vessel. A balloon-expandable stent is delivered to a desired location within a coronary artery in a contracted condition on a balloon of a catheter and then expanded to a larger diameter by expansion of the balloon. The balloon is deflated to remove the catheter with the stent remaining in place within the artery at the site of the dilated lesion.

In the design of catheter balloons, balloon characteristics such as strength (e.g., rupture pressure), flexibility, and compliance are tailored to provide the desired performance for a particular application. In stent applications, additional performance characteristics including stent retention, shredding and pin hole resistance, stent dislodgement force, and refold after stent deployment are also considered. Angioplasty and stent delivery balloons preferably have high strength (i.e., high rupture pressure) for inflation at relatively high pressure, and high flexibility and softness for improved ability to track the tortuous anatomy and cross lesions. The balloon compliance, which depends on factors such as the nature of the balloon material, the balloon wall thickness, and processing conditions, is established to provide the balloon with the desired amount of expansion during inflation. Compliant balloons, for example balloons made from materials such as polyethylene, exhibit substantial stretching upon the application of tensile force. Noncompliant balloons, for example balloons made from materials such as PET, exhibit relatively little stretching during inflation, and therefore provide controlled radial growth in response to an increase in inflation pressure within the working pressure range. However, noncompliant balloons generally have relatively low flexibility and softness. As such, it is difficult to provide a low compliant balloon with high flexibility and softness for enhanced catheter trackability.

As such, there is a need for a catheter balloon with high strength and limited compliance, yet with excellent ability to track within the patient's vasculature and cross lesions therein. Likewise a balloon having good stent retention, shredding and pin hole resistance, stent dislodgement force and refold after stent deployment is needed for stent applications. The disclosed subject matter satisfies these and other needs.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a multilayer balloon for a catheter. The balloon comprises a first layer made of a first polymer material having a first Shore durometer hardness, a second layer made of a second polymer material having a second Shore durometer hardness greater than the first Shore durometer hardness, wherein the second layer is an inner layer relative to the first layer, and a third layer made of a third polymer material having a third Shore durometer hardness less the first Shore durometer hardness, wherein the third layer is an inner layer relative to the second layer.

In some embodiments, the multilayer balloon, as blown, has a nominal working diameter. The balloon can have a noncompliant limited radial expansion beyond the nominal working diameter at pressures above a nominal pressure. For example, the multilayer balloon, as blown, can have a compliance less than about 0.035 mm/atm between a nominal pressure and a rated burst pressure. Alternatively, the balloon can have a semicomplaint radial expansion beyond the nominal working diameter at pressures above a nominal pressure.

In some embodiments, the multilayer balloon, as blown, can have a balloon wall thickness less than 0.003 inch, 0.002 inch, or 0.001 inch. The multilayer balloon, as blown, can have a rated burst pressure between about 15 to about 30 atm.

In some embodiments, at least the third layer is substantially at a third layer maximum blow-up-ratio when the multilayer balloon is substantially at the nominal working diameter. Alternatively, at least the third layer is at a blow up ratio of at least about 80%, or even 90%, of a third layer maximum blow-up-ratio when the multilayer balloon is substantially at the nominal working diameter. The third layer can have a blow-up-ratio between about 7.0 and about 8.0, or between about 7.2 and about 7.8.

In some embodiments, the second layer can be at a blow up ratio of at least 80% or 70% of a second layer maximum blow-up-ratio when the multilayer balloon is substantially at the nominal working diameter. Furthermore, the first layer can be at a blow up ratio of at least 60% of a first layer maximum blow-up-ratio when the multilayer balloon is substantially at the nominal working diameter.

The multilayer balloon can further comprise an expandable stent mounted on an outer surface of the multilayer balloon.

In one embodiment, the first Shore durometer hardness can be about 70D. The second Shore durometer hardness can be about 72D or greater. The third Shore durometer hardness can be less than about 70D.

In one embodiment, the first Shore durometer hardness can be about 70D, the second Shore durometer hardness can be about 72D, and the third Shore durometer hardness can be about 63D. The first polymer material can be a polyether block amide, the second polymer material can be a polyether block amide, and the third polymer material can be a polyether block amide. The balloon can have a semicompliant radial expansion beyond the nominal working diameter at pressures above a nominal pressure.

Alternatively, the first Shore durometer hardness can be about 70D, the second Shore durometer hardness can be about 74D or greater, and the third Shore durometer hardness can be about 63D. The first polymer material can be a polyether block amide, the second polymer material can be nylon, and the third polymer material can be a polyether block amide. The balloon can have a noncompliant limited radial expansion beyond the nominal working diameter at pressures above a nominal pressure.

In another embodiment, the first Shore durometer hardness can be between about 70D and about 72D, the second Shore durometer hardness can be about 74D or greater, and the third Shore durometer hardness is between about 63D and about 70D.

In one embodiment, the third layer can define an inner surface of the balloon. The first layer can define an outer surface of the balloon. The first layer, the second layer, and the third layer can be coextruded.

In accordance with another aspect of the disclosed subject matter, a method of making a multilayer balloon for a catheter is provided. The method includes providing a tube having at least a first layer, a second layer, and a third layer. The first layer is made of a first polymer material having a first Shore durometer hardness. The second layer is made of a second polymer material having a second Shore durometer hardness greater than the first Shore durometer hardness. The second layer is an inner layer relative to the first layer. The third layer is made of a third polymer material having a third Shore durometer hardness less the first Shore hardness, wherein the third layer is an inner layer relative to the second layer. The method also includes radially expanding the tube in a mold to form a balloon having a nominal working diameter.

In some embodiments, the tube can be formed by coextruding the first layer, the second layer, and the third layer.

The tube can be radially expanded in the mold via a single blow process. Alternatively, the tube can be radially expanded in the balloon via a double blow process.

In accordance with one aspect of the disclosed subject matter, a balloon catheter is provided. The balloon catheter includes an elongate catheter shaft having a proximal section, a distal section, and an inflation lumen defined therein and a multilayer balloon on the distal section of the shaft. The balloon comprises a first layer made of a first polymer material having a first Shore durometer hardness, a second layer made of a second polymer material having a second Shore durometer hardness greater than the first Shore durometer hardness, wherein the second layer is an inner layer relative to the first layer, and a third layer made of a third polymer material having a third Shore durometer hardness less the first Shore durometer hardness, wherein the third layer is an inner layer relative to the second layer. The balloon catheter can further include an expandable stent mounted on an outer surface of the multilayer balloon.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

FIG. 1 is a side view, partially in section, of an over-the-wire stent delivery balloon catheter in accordance with the disclosed subject matter.

FIG. 2 is a transverse cross-sectional view of the catheter of FIG. 1 taken along line 2-2.

FIG. 3 is a transverse cross-sectional view of the catheter of FIG. 1 taken along line 3-3.

FIG. 6 is a table of data for examples of various multilayer balloons in accordance with the disclosed subject matter.

FIGS. 7 to 10 are graphs depicting the compliance of various multilayer balloons in accordance with the disclosed subject matter.

FIG. 11 is a graph depicting the compliance of a control balloon.

DETAILED DESCRIPTION OF THE PREFERRED EMBODIMENTS

The devices and methods presented herein can be used for a variety of treatment within various lumens of a patient. For example, the disclosed subject matter is suited for treatment of the cardiovascular system of a patient, such as performance of angioplasty and delivery of a therapeutic agent and/or a stent to a vasculature.

In accordance with the disclosed subject matter, a multilayer balloon for a catheter is provided comprising a first layer made of a first polymer material having a first Shore durometer hardness, a second layer made of a second polymer material having a second Shore durometer hardness greater than the first Shore durometer hardness, wherein the second layer is an inner layer relative to the first layer, and a third layer made of a third polymer material having a third Shore durometer hardness less the first Shore durometer hardness, wherein the third layer is an inner layer relative to the second layer. Furthermore, a method is provided comprising providing a tube having at least a first layer, a second layer, and a third layer. The first layer is made of a first polymer material having a first Shore durometer hardness. The second layer is made of a second polymer material having a second Shore durometer hardness greater than the first Shore durometer hardness. The second layer is an inner layer relative to the first layer. The third layer is made of a third polymer material having a third Shore durometer hardness less the first Shore hardness, wherein the third layer is an inner layer relative to the second layer. The method also includes radially expanding the tube in a mold to form a balloon having a nominal working diameter.

Reference will now be made in detail to the preferred embodiments of the disclosed subject matter, an example of which is illustrated in the accompanying drawing. The method and corresponding steps of the disclosed subject matter will be described in conjunction with the detailed description of the system.

Figure 4:
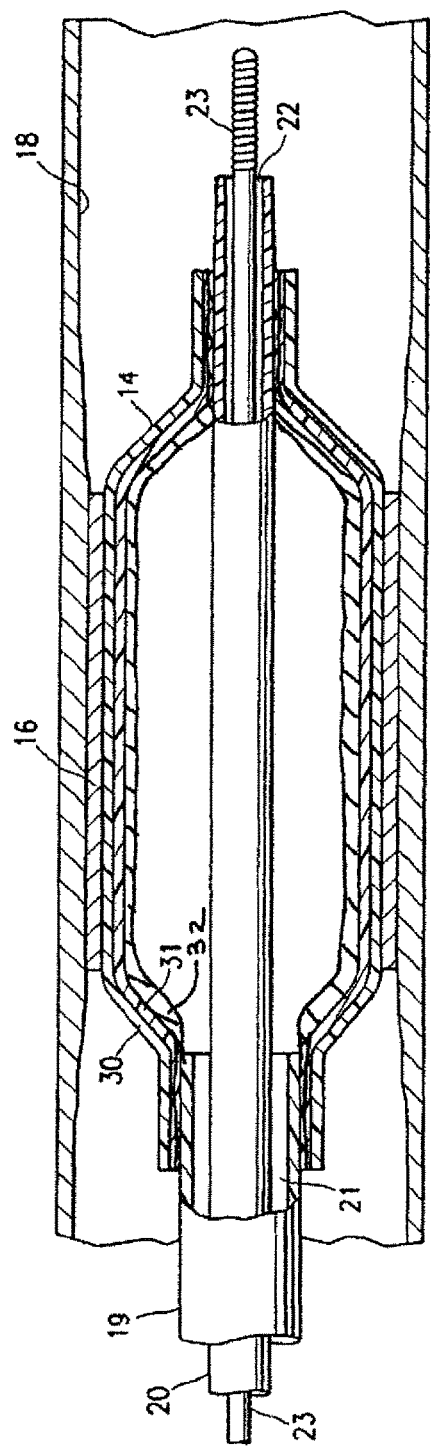
FIG. 4 illustrates the balloon catheter of FIG. 1 with the balloon inflated within a vessel.

For the purpose of illustration and not limitation, FIG. 1 illustrates a representative embodiment of a balloon catheter 10 in accordance with the disclosed subject matter. The catheter includes an elongated catheter shaft 11 having a proximal section 12, a distal section 13, an inflation lumen 21 defined therein, and a guidewire lumen 22 configured to slidably receive a guidewire 23 therein. The shaft 11 has a multilayer balloon 14 disposed on the distal shaft section. An adapter 17 on a proximal end of the catheter shaft provides access to the guidewire lumen 22, and has an arm 24 configured for connecting to a source of inflation fluid (not shown). FIG. 1 illustrates the balloon in a noninflated configuration for advancement within a patient's body lumen 18. As embodied in FIG. 1, the balloon catheter can be a stent delivery catheter and can include a radially expandable stent 16 mounted on an outer surface of the multilayer balloon 14 for delivery and deployment within the body lumen 18. The balloon catheter 10 is advanced in the body lumen 18 with the balloon 14 in the noninflated configuration, and the balloon inflated by introducing inflation fluid into the balloon interior to expand the balloon 14 and stent 16 mounted thereon. FIG. 4 illustrates the balloon catheter 10 with the balloon in the inflated configuration to expand the stent against the wall of the body lumen 18. The balloon 14 is then deflated to allow for repositioning or removal of the catheter from the body lumen 18, with the stent 16 implanted in the body lumen 18.

As embodied herein, the shaft comprises an outer tubular member 19 and an inner tubular member 20 positioned in the outer tubular member 19. The inner tubular member 20 has a guidewire lumen 22 defined therein, and an inflation lumen 21 is defined by the annular space between the inner surface of the outer tubular member 19 and the outer surface of the inner tubular member 20, as best shown in FIG. 2 illustrating a transverse cross section of the catheter of FIG. 1 taken along line 2-2, for the purpose of illustration and not limitation. Alternatively, the shaft can be configured as a dual lumen monolithic member with each of the guidewire lumen 22 and the inflation lumen 21 extending in parallel. Additionally the shaft can be configured and constructed of multiple tubular members along its length for varied rigidity and flexibility as is known. Furthermore, and as an alternative to the over-the-wire configuration, a rapid exchange configuration can be provided if desired. A variety of suitable catheter shaft configurations can be used and are disclosed in U.S. Patent Publication No. 2009/0156998 filed Dec. 17, 2007, U.S. Patent Publication No. 2008/0045928 filed Jun. 15, 2007, and U.S. Pat. No. 7,906,066, filed Jun. 30, 2006, each of which is incorporated in its entirety by reference herewith.

The balloon of the disclosed subject matter can have a variety of suitable shapes and configurations. For the purpose of illustration and not limitation, the balloon 14 embodied herein and depicted in FIG. 1 has a proximal skirt section sealingly secured to the distal end of the outer tubular member 19, and a distal skirt section sealingly secured to a distal end of the inner tubular member 20, to define an interior 15 of the balloon in fluid communication with the inflation lumen 21 of the shaft. FIG. 3 illustrates a transverse cross section of the catheter of FIG. 1 taken along line 3-3, although the space between the inner surface of the noninflated balloon and the outer surface of the portion of the shaft 11 therein is somewhat exaggerated in FIGS. 1 and 3, for ease of illustration.

Although not illustrated, the multilayer balloon 14 in accordance with the disclosed subject matter can have a noninflated configuration with folds or wings, which can be wrapped around the balloon to form a low profile configuration for introduction and advancement within a patient's body lumen. As a result, the multilayer balloon inflates to a nominal working diameter by unfolding of the wings when the interior of the balloon is inflated with inflation medium.

As previously noted and in accordance with one embodiment of the disclosed subject matter, the multilayer balloon 14 has a first layer 30, a second layer 31 which is an inner layer relative to the first layer 30, and a third layer 32 which is an inner layer relative to the second layer 31. The first layer 30 is made of a first polymer material having a first Shore durometer hardness, the second layer 31 is made of a second polymer material having a second Shore durometer hardness, and the third layer 32 is made of a third polymer material having a third Shore durometer hardness. The second Shore durometer hardness is greater than the first Shore durometer hardness, and the first Shore durometer hardness is greater than the third Shore durometer hardness (i.e., the third Shore durometer hardness is less than both the first Shore durometer hardness and the second Shore durometer hardness). As shown, the third layer 32 defines an inner surface of the balloon and the first layer 30 defines an outer surface of the balloon. Although only three layers are depicted for purpose of illustration, it is recognized that additional layers can be provided.

Particularly, it is noted that the Shore durometer hardness of the multilayer balloon disclosed herein is staggered between the outer layer and the inner layer, which provides for unique and unexpected results. That is, prior multilayered balloons with layers of polymers having different strengths/hardnesses are arranged either with progressively increasing or decreasing durometer hardnesses from the inner to the outer layer. By contrast, the multilayer balloon in accordance with the disclosed subject matter has various layers of polymers with Shore durometer hardnesses in a staggered configuration with the lowest hardness located at a third (e.g., inner) layer and the highest hardness is located at a second (i.e., intermediate) layer, with an intermediate hardness located at a first (e.g., outer) layer.

This staggered configuration provides unique and surprising results as set forth in greater detail below. Generally, the presence of a lower durometer material to form the inner layer(s) of the balloon was not expected to provide a relatively higher strength balloon, at least because the rupture pressure and compliance of a balloon are affected by the strength (e.g., hoop strength) of a balloon and a softer material generally has a relatively lower hoop strength. However, a multilayered balloon in accordance with the disclosed subject matter unexpectedly results in a high strength balloon. At the same time, the presence of the lower durometer material inner layer provides increased softness and more flexibility and thus a better ability to track than a balloon formed of 100% of the highest durometer material.

A variety of suitable materials with appropriate Shore durometer hardness can be used to form each of the first, second, and third layers 30, 31, and 32 including but not limited to polyamides, polyurethanes, and polyesters. For example and not limitation, in one embodiment, at least one of the layers is formed of an elastomer to provide a relatively low flexural modulus for balloon flexibility. Elastomeric polymers suitable for forming the first, second and/or third layer of the multilayered balloon generally have a flexural modulus of about 40 kpsi to about 110 kpsi. Thus, unlike nonelastomeric materials such as PET which have been used in the past to provide relatively low compliance catheter balloons, multilayered noncompliant balloons in accordance with certain embodiments of the disclosed subject matter are formed of one or more elastomers to provide improved balloon flexibility. Presently preferred materials are from the same polymeric family/class such as polyamides including nylons and polyether block amides.

For example, in one embodiment, the multilayered balloon first layer is formed of a polyether block amide (PEBA) material (e.g., commercially available as PEBAX®) having a Shore durometer hardness of about 70D, while the second layer is formed of a PEBA material having a higher Shore durometer hardness of about 72D or greater, and the third layer is formed of a PEBA material having a lower Shore durometer hardness of less than about 70D and preferably about 63D. In one embodiment, the first Shore durometer hardness is about 70D, the second Shore durometer hardness is about 72D, and the third Shore durometer hardness is about 63D. In such an embodiment, the balloon can have a semicomplaint radial expansion beyond the nominal working diameter at pressures above a nominal pressure.

In an alternate embodiment, the first Shore durometer hardness can be about 70D, the second Shore durometer hardness can be about 74D or greater, and the third Shore durometer hardness can be about 63D. In this embodiment, the first polymer material can be a polyether block amide, the second polymer material can be nylon, and the third polymer material can be a polyether block amide and the balloon can a noncompliant limited radial expansion beyond the nominal working diameter at pressures above a nominal pressure. The nylon can be, for example, Grillamid L25 Nylon 12 having a hardness of 74D. In another embodiment, the first Shore durometer hardness is between about 70D and about 72D, the second Shore durometer hardness is about 74D or greater, and the third Shore durometer hardness is between about 63D and about 70D. In this embodiment, simulated arterial modeling testing demonstrates superior delivery performance using a first Shore durometer hardness of 70D as compared to 72D.

As embodied herein, the multilayer balloon, as blown, has a balloon double wall thickness less than about 0.003 inch. Particularly, a balloon double wall thickness of less than 0.002 inch, and even less than 0.001 inch, is provided. In accordance with one embodiment, the second (i.e., intermediate) layer can have a greater wall thickness than the adjacent layers. For example, and not limitation, the second layer can make up about 30% to about 65% of the total wall thickness of the multilayered balloon. In one embodiment, prior to expansion in a mold, the first and third layers of a three-layer balloon each can have a thickness of about 2 mil while the second layer of the three-layer balloon can have a thickness of about 6.25 mil. As such, the second (i.e., intermediate) layer having the greatest hardness and greatest thickness can be the load bearing layer for the balloon. In this manner, the thickness of the second intermediate layer can be modified to control the rupture pressure of the balloon, with increasing thickness generally resulting in increased rupture pressure.

By contrast, the first (e.g., outer) layer can be selected to provide various performance characteristics. For example, having a first (e.g., outer) layer having a Shore durometer hardness less than the immediately adjacent second (i.e., intermediate) layer but not as soft as the third (e.g., inner) layer, can facilitate embedding the stent 16 into the outer surface of the balloon for improved stent retention. Furthermore, such a configuration is demonstrated to provide improved shredding and pin-hole resistance and improved rewrap thus reducing the withdrawal force required after stent deployment as described in detail by example below. Additionally, having the first (e.g., outer) layer of intermediate hardness has been demonstrated by Example to act a spacer or shock absorber to prevent over expansion of the second (i.e., intermediate) layer, which being of the highest hardness can be more susceptible to failure (e.g., shredding).

Thus, by selecting the polymeric materials forming the balloon layers and arranging and radially expanding the multiple layers of the balloon in accordance with the disclosed subject matter, a multilayer balloon is provided having a surprising improved combination of characteristics including high strength, low compliance, high flexibility and ability to track, and good stent retention, shredding and pin hole resistance, stent dislodgement force and refold after stent deployment. Such combinations of characteristics are demonstrated in the data and graphs below.

Additionally or alternatively, in one embodiment, the balloon can have a very thin total wall thickness for improved low profile and flexibility due to the thinner walls of the balloon. However, despite the thin wall, the multilayer balloon as disclosed herein still provides a high rupture pressure and good stent performance characteristics.

In view of the above, and in accordance with the disclosed subject matter, the multilayered balloon can provide a very low compliance for controlled balloon expansion, without compromising relatively high flexibility and softness for excellent ability to track the patient's vasculature and cross lesions. As a result, the balloon catheter of the disclosed subject matter has improved performance due to the flexibility, softness, and controlled expansion of the balloon. The compliance of the balloon should be understood to refer to the degree to which the polymeric wall of the balloon stretches/distends as the balloon expands beyond the nominal diameter of the balloon with increasing inflation pressure above nominal pressure (i.e., the inflation pressure required to inflate the balloon to the nominal working diameter). For example, a compliance curve can be provided to demonstrate the balloon outer diameter as a function of increasing inflation pressure in millimeters/atmospheres (mm/atm), wherein a flatter or more horizontal curve or section of the curve indicates a lower compliance than a steeper curve. The compliance is typically determined for the pressure range extending from the nominal pressure (i.e., the pressure required to inflate the molded volume of the balloon to the blow-molded nominal diameter) to the burst pressure or the rated burst pressure of the balloon. The rated burst pressure (RBP), calculated from the average rupture pressure, is the pressure to which 99.9% of the balloons can be pressurized without rupturing, with 95% confidence. The term "noncompliant" is generally understood to mean a balloon with compliance of not greater than about 0.035 mm/atm, preferably not greater than about 0.025 mm/atm, between a nominal pressure and a rated burst pressure. By contrast, compliant balloons typically have a compliance of at least about 0.045 mm/atm or greater. The term semicomplaint therefore is understood to mean a balloon with compliance of between about 0.025 and about 0.04 mm/atm.

In accordance with some embodiments of the disclosed subject matter, the balloon can expand a very small amount (i.e., noncompliantly) at pressures above the nominal pressure. Such a balloon has a noncompliant limited radial expansion beyond the nominal working diameter at pressures above a nominal pressure. As a result, the balloon can be configured to reduce injury to a patient's blood vessel. Alternatively, the balloon can have a semicomplaint radial expansion beyond the nominal working diameter at pressures above a nominal pressure if desired.

For proposes of illustration and not limitation, in one embodiment the multilayered balloon 14 can have a nominal pressure of about 8 to about 12 atm. The multilayer balloon, as blown, can have a rated burst pressure of about of about 15 to about 30 atm. The multilayered balloon can reach the nominal diameter of the balloon at about 8 to about 12 atm, and thereafter increase in diameter in a noncompliant manner with a compliance of about 0.015 to about 0.035 mm/atm within the working pressure range (e.g., between about 8-12 atm to about 15-30 atm) of the multilayered balloon to a diameter which is not more than about 25% greater than the nominal diameter.

The overall dimensions of catheter can be selected to accommodate a variety of needs including the size of the balloon and guidewire to be employed, the catheter type, and the size of the artery or other body lumen through which the catheter must pass, and/or the size of the stent being delivered. For example, and with reference to PTCA catheters and coronary stent delivery systems, the outer tubular member has an outer diameter of about 0.025 to about 0.04 inch (0.064 to 0.1 cm), usually about 0.037 inch (0.094 cm), and the wall thickness of the outer tubular member 19 can vary from about 0.002 to about 0.008 inch (0.0051 to 0.02 cm), typically about 0.003 to 0.005 inch (0.0076 to 0.013 cm). The inner tubular member 20 typically has an inner diameter of about 0.01 to about 0.038 inch (0.025 to 0.1 cm), usually about 0.016 to 0.038 inch (0.04 to 0.1 cm), and a wall thickness of about 0.004 to about 0.008 inch (0.01 to 0.02 cm). The overall length of the catheter 10 can range from about 100 to about 150 cm, and is typically about 143 cm. Preferably, balloon 14 has a length about 0.8 cm to about 6 cm, and an inflated working diameter of about 2 to about 5 mm.

The various components can be joined using conventional bonding methods such as by fusion bonding or use of adhesives. Although the shaft is illustrated as having an inner and outer tubular member, a variety of suitable shaft configurations can be used including a dual lumen extruded shaft having a side-by-side lumens extruded therein.

In accordance with another aspect of the disclosed subject matter and as previously noted, a method of making the multilayer balloon for a catheter is provided. For purpose of illustration and not limitation, reference is made to the schematic embodiment of FIGS. 1 and 5. The method comprises providing a multilayer tube. The multilayered tube includes a first layer 30, a second layer 31 as an inner layer relative to the first layer 30, and a third layer 32 as an inner layer relative to the second layer 31. The first layer 30 is made of a first polymer material having a first Shore durometer hardness, the second layer 31 is made of a second polymer material having a second Shore durometer hardness, and the third layer 32 is made of a third polymer material having a third Shore durometer hardness. The second Shore durometer hardness is greater than the first Shore durometer hardness, which is greater than the third Shore durometer hardness (i.e., the third Shore durometer hardness is less the first Shore durometer hardness). The tube can be formed by coextrusion of all layers together, although a variety of other suitable conventional methods can be used. For example, the first layer and/or the second layer can be extruded sequentially onto the third layer. Alternatively, one or more layers can be added to an extruded or coextruded tube for example by heat shrinking, dip coating, adhesive or fusion bonding, frictionally engaging, or nesting the additional layer(s) to the tube.

Figure 5:
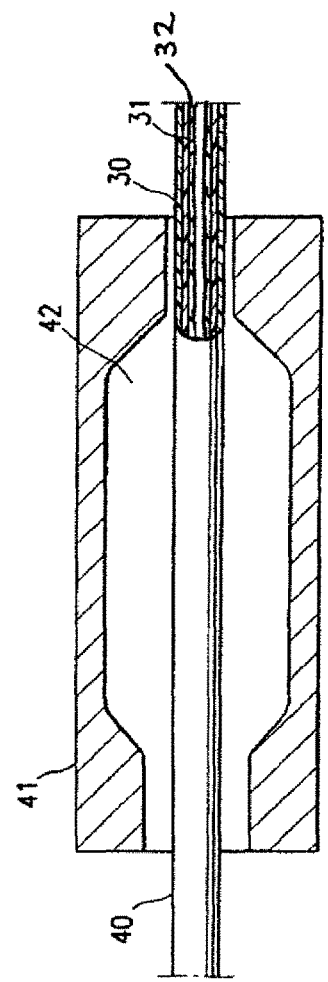
FIG. 5 is a partial cross-sectional side view of a multilayer balloon tubing in a mold prior to being radially expanded therein accordance with the disclosed subject matter.

The multilayered tube is then radially expanded in a mold to form the balloon 14 having a nominal working diameter. FIG. 5 illustrates the multilayered tube 40 in a mold 41 having an interior chamber 42 with a shape configured to form the balloon 14, and an inner diameter about equal to the nominal working diameter of the expanded balloon 14. The multilayered tube 40 is typically stretched axially and heated during blow molding in the mold, as is conventionally known. For example, in one embodiment, the tube is longitudinally stretched by about 100 to about 250% during blow molding, which produces a biaxially oriented balloon. The single wall thickness of the tube (prior to being radially expanded in the mold) is about 0.005" (0.25 mm) to about 0.015" (0.75 mm), and the single wall thickness of the resulting balloon (radially expanded in the mold) is about 0.001" (0.025 mm) to about 0.002" (0.050 mm), depending on the desired balloon characteristics and uses. The resulting multilayered balloon has an inflated shape corresponding to the inner surface of the mold and an outer diameter, e.g., nominal working diameter, about equal to the inner diameter of the mold.

The blow-up-ratio (BUR) of the balloon formed from a polymer tube should be understood to refer to the ratio of the outer diameter of the blown balloon expanded within the mold (i.e., the mold inner diameter) to the inner diameter of the polymer tube prior to being expanded in the mold, as described in detail in U.S. Pat. No. 7,828,766, filed Dec. 20, 2005, which is incorporated in its entirety by reference herewith. Each individual layer of the multilayered balloon similarly has its own BUR based on the ratio of the inner diameter of the mold and the inner diameter (prior to expansion in the mold) of the layer of the polymeric tube. For a given balloon wall thickness, the rupture strength generally increases and the radial compliance decreases as the balloon BUR increases. The maximum attainable BUR of a polymeric material can be determined experimentally, although characteristics such as the ultimate tensile strength and elongation to break of the material can be indicative at least for some materials (e.g., a material having a relatively higher ultimate tensile strength and elongation to break is expected, in general, to have a higher maximum BUR).

In accordance with one aspect of the disclosed subject matter, the materials and dimensions of the multilayered tube and mold can be selected so that at least the third (e.g., inner) layer of the resulting balloon is radially expanded to substantially its maximum possible amount, i.e. the maximum BUR of the balloon layer. In this manner, a balloon with noncompliant behavior and high strength can be provided. Thus, the third layer can be substantially at a third layer maximum blow-up-ratio when the multilayer balloon is substantially at the nominal working diameter. Alternatively, the third layer is at a blow-up-ratio at least about 80%, or even 90% of a third layer maximum blow-up-ratio when the multilayer balloon is substantially at the nominal working diameter. The third layer can have a blow-up-ratio between about 7.0 and about 8.0, or even more particularly between about 7.2 and about 7.8

If a highly non-compliant balloon is desired, each layer (e.g., first, second, and third layers) can be at its maximum BUR, so that the balloon has layers of highly oriented material and, consequently, a very low compliance. In such an embodiment, the inner diameter of each layer of the multilayered tube is selected so that the ratio of the inner diameter of the mold and the inner diameter of the layer of the multilayered tube (prior to being radially expanded in the mold) can be substantially at a maximum blow-up-ratio for the polymeric material forming the layer. Alternatively, the second layer can be at a blow-up-ratio at least 70%, or even 80%, of a second layer maximum blow-up-ratio when the multilayer balloon is substantially at the nominal working diameter. Likewise the first layer can be at a blow-up-ratio at least 60% of a first layer maximum blow-up-ratio when the multilayer balloon is substantially at the nominal working diameter.

As embodied herein, the tube can be radially expanded in the mold via a single blow process. Alternatively, the tube can be radially expanded in the mold via a double blow process. Generally, this process involves radially expanding a multilayer tube in a first mold having an intermediate size smaller than the nominal working diameter of the desired balloon. The tube may be radially expanded using an inflation medium as is known in the art. Next the expanded multilayer tube is transferred to a second mold having a size corresponding to the nominal working diameter of the balloon. The tube is then radially expanded to the nominal working diameter of the desired balloon. This so-called "double-blow" method can help to make the initiation event during balloon expansion less severe and enables the processing of balloons possessing a greater overall BUR value at their innermost surface. The double-blow process is described in more detail in U.S. Patent Publication No. 2002/0171180 filed May 21, 2001, U.S. Patent Publication No. 2012/0065718 filed Sep. 14, 2010, and U.S. Pat. No. 6,620,127, filed Dec. 1, 1999, each of which is incorporated in its entirety by reference herewith.

EXAMPLES

While the subject matter is capable of various modifications and alternative forms, specific embodiments thereof have been shown by way of examples, and will herein be described in detail. It should be understood, however, that it is not intended to limit the subject matter to the particular forms disclosed but, on the contrary, the intention is to cover all modifications, equivalents, and alternatives falling within the spirit and scope of the subject matter as defined by the appended claims.

The following examples are presented for purposes of illustration and description. These examples are representative but not dispositive and are not intended to be exhaustive or to limit the disclosed subject matter to those embodiments disclosed.

Multilayered balloon tubings having first, second, and third layers were coextruded having the overall dimensions provided in FIG. 6, in accordance with the disclosed subject matter. The materials used of each layer are provided in FIG. 6. The tubing was blow-molded by heating and pressurizing the tubing in a mold having the dimension provided in FIG. 6 using a single or double blow cycle and blow-up-ratio as specified in FIG. 6. The resulting multilayered balloons have the size, double wall thickness, compliance, rupture pressure, axial growth, and hoop strength specified in FIG. 6.

The compliance, rupture pressure, axial growth, and hoop strength of the multilayered balloons were compared to a control balloon similarly formed and with approximately the same wall thickness but from a single layer (100%) of the 72D PEBAX. The control balloon was blow-molded in a 0.116 inch ID mold, using a single blow process and a balloon tubing extruded to a 0.018 inch ID and a 0.0365 inch OD, to form a balloon having the desired wall thickness. The resulting control balloon had an average double wall thickness of 1.52 mil and a BUR of 6.44. The multilayered balloons in accordance with the disclosed subject matter and the control monolithic balloon each had a rupture pressure of greater than 25 atm and a hoop strength greater than 30,000 psi. Thus surprisingly and despite the presence of the lower durometer material for the inner and outer layers, the multilayer balloons in accordance with the disclosed subject matter have about the same or higher rupture pressure and hoop strength than the balloon made solely of PEBAX 72D.

The compliance curves of the multilayered balloons in accordance with the disclosed subject matter are shown in FIGS. 7-10 and the compliance curve for the control is shown in FIG. 11. Each compliance curve was generated by inflating a balloon subassembly and measuring the change in the balloon outer diameter in response to increasing inflation pressures. As illustrated in FIG. 6, the compliance slope from 12 to 20 atm for each of the multilayered balloons in accordance with the disclosed subject matter is less than that of the monolithic control balloon. Thus surprisingly and despite the presence of the lower durometer material for the inner and outer layers, such that the 72D PEBAX made up a smaller percentage of the wall thickness of the balloon than in the monolithic balloon made solely of 72D PEBAX, the multilayered balloons of the disclosed subject matter had a lower compliance.

As can be seen in FIG. 6, utilizing a double blow process in accordance with the disclosed subject matter can increase the rupture pressure and decrease the compliance of the multilayer balloon. For example, multilayer balloon samples 1 and 2 were both made from the same extruded tube but sample 2 was prepared using a double blow process which increased the rupture pressure of the balloon from about 27 to about 29 atm and decreased the compliance slope from about 0.019 to about 0.014.

Figure 12:
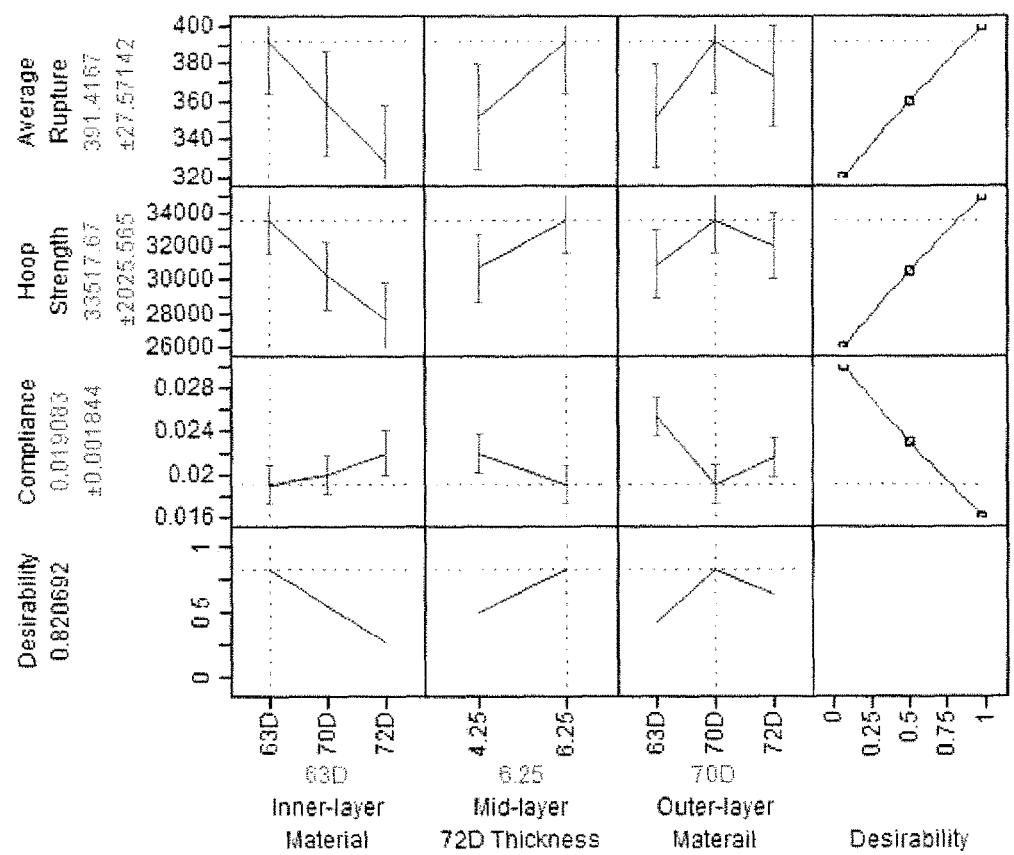
FIG. 12 is a series of graphs showing the compliance, hoop strength, average rupture, and desirability of multilayer balloons in accordance with the disclose subject matter as compared to alternative multilayer balloon configurations.

A variety of tests were performed to compare balloons in accordance with the disclosed subject matter to alternative multilayer balloon arrangements. For example, the compliance, hoop strength, and average rupture of multilayered balloons in accordance with the disclosed subject matter were compared to alternative trilayer balloon configurations similarly formed but with varying Shore durometer hardnesses for the inner and outer layers, as shown in FIG. 12. That is, testing was performed using three different materials for the inner layer, two different thickness for the intermediate layer, and three different materials for the outer layer.

Thus the graphs in the first three columns of FIG. 12 represent various measurements for balloons made of PEBAX 63D, PEBAX 70D, or PEBAX 72D as an inner layer, PEBAX 72D as an intermediate layer at two different thicknesses, and PEBAX 63D, PEBAX 70D, or PEBAX 72D as the outer layer.

The graphs in the fourth column of FIG. 12 (i.e. the right-most graphs labeled "Desirability") qualitatively shows the desirability of each performance characteristic tested. For example, it is most desirable (i.e. desirability=1) to have a high average rupture pressure and least desirable (i.e. desirability=0) to have a low average rupture pressure. Similarly, it is most desirable (i.e. desirability=1) to have a high hoop strength and least desirable (i.e. desirability=0) to have a low hoop strength. Finally, it is most desirable (i.e. desirability=1) to have a low compliance and least desirable (i.e. desirability=0) to have a high compliance.

As shown for the inner layer material in FIG. 12 (i.e. the left-most graphs labeled "Inner-layer Material"), the lower the Shore durometer hardness of the inner layer, the better the performance as demonstrated by higher average rupture and hoop strength and lower compliance. Thus the desirability (i.e., the bottom left graph in FIG. 12) is highest when the Shore durometer hardness of the inner layer is 63D, as the average rupture and hoop strength is higher and the compliance is lower.

As shown for the intermediate layer in FIG. 12 (i.e. the graphs labeled "Mid-layer 72D Thickness"), selecting a greater thickness for the intermediate layer results in better performance as demonstrated by higher average rupture and hoop strength and lower compliance. Thus the desirability (i.e., the bottom graph in the "Mid-layer 72D Thickness" column) is highest for the thicker intermediate layer, as the average rupture and hoop strength is higher and the compliance is lower.

As shown for the outer layer material in FIG. 12 (i.e. the graphs labeled "Outer-layer Material"), an intermediate Shore durometer hardness value provides better performance as shown by higher average rupture and hoop strength and lower compliance. Thus the desirability (i.e., the bottom graph in the "Outer-layer Material" column) is highest when the Shore durometer hardness of the outer layer is 70D, as the average rupture and hoop strength is higher and the compliance is lower.

As demonstrated by the various graphs of FIG. 12, the staggered configuration in accordance with the disclosed subject matter provides unique and surprising results. For example, the desirability for the outer layer material (i.e., the bottom graph in the "Outer-layer Material" column) unexpectedly shows an inflection point or peak in performance (e.g. average rupture, hoop strength, and compliance) at a Shore durometer hardness that is between the Shore durometer hardness of the inner and intermediate layers. The same inflection point or peak is present in the graphs for the average rupture, hoop strength, and compliance of the outer layer material; all of which demonstrate the superior unexpected results for balloons in accordance with the disclosed subject matter. Particularly, having the outer layer material with a Shore durometer hardness between that of the inner and intermediate layers in accordance with the disclosed subject matter results in a average rupture pressure of at least about 390 psi. Similarly, having an outer layer material with a Shore durometer hardness between that of the inner and intermediate layers in accordance with the disclosed subject matter results in a hoop strength of at least about 33,500 psi. Additionally, having an outer layer material with a Shore durometer hardness between that of the inner and intermediate layers in accordance with the disclosed subject matter results in a compliance less than about 0.02 mm/atm. These results are surprising at least because one would expect a higher durometer material for the outer layer would increase the average rupture and hoop strength and decrease the compliance because the rupture pressure and compliance of a balloon are affected by the strength (e.g., hoop strength) of a balloon and a softer material generally has a relatively lower hoop strength.

The stent performance characteristics of multilayer balloons in accordance with the disclosed subject matter were also measured. For example, the stent retention peak force was measured for sample 1 to be about 1.61 lbf, which compares favorably to a control two layer balloon made of a PEBAX 72D outer layer and a PEBAX 63D inner layer having a stent retention peak force of about 1.48 lbf. Likewise, balloon rewrap was also tested by advancing a balloon with a crimped stent into a 0.045" hole gage, allowing the balloon to soak 15 seconds, inflating the balloon to nominal pressure (10 atm), pulling and holding negative pressure for 30 seconds, removing the stent, checking for trifold, pulling back through 0.045" hole gage, and advancing the folded balloon to a 0.044" hole gage. The multilayer balloon in accordance with the disclosed subject matter refolded into the trifold configuration 5 out of 5 times and was able to cross the 0.044" hole gage 5 out of 5 times, whereas a single layer control balloon of PEBAX 72D refolded into the trifold configuration 4 out of 5 times and was only able to cross the 0.044" hole gage 4 out of 5 times and a two layer control balloon made of a PEBAX 72D outer layer and a PEBAX 63D inner layer refolded into the trifold configuration only 3 out of 5 times and was only able to cross the 0.044" hole gage 3 out of 5 times.

While the disclosed subject matter is described herein in terms of certain preferred embodiments, those skilled in the art will recognize that various modifications and improvements can be made to the disclosed subject matter without departing from the scope thereof. For example, in the illustrated embodiment described above, the first layer defines an outer surface of the balloon and the third layer defines an inner surface of the balloon. However, the balloon of the disclosed subject matter can alternatively have one or more additional layers (not shown). Additional layer(s) can increase the dimensions of the tube or balloon formed therefrom to a desired value, and/or can be used to provide an inner or outer surface of the balloon with a desired characteristic. Therefore, it should be understood that the balloon 14 of the disclosed subject matter discussed below has at least three layers, and optionally includes one or more additional layers, unless otherwise noted as having a specified set number of layers.

Various designs for balloon catheters well known in the art can be used in the catheter system of the disclosed subject matter. For example, conventional over-the-wire balloon catheters for angioplasty or stent delivery usually include a guidewire receiving lumen extending the length of the catheter shaft from a guidewire proximal port in the proximal end of the shaft to a guidewire distal port in the catheter distal end. Rapid exchange balloon catheters for similar procedures generally include a relatively short guidewire lumen extending from a guidewire port located distal to the proximal end of the shaft to the catheter distal end.

Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

The invention claimed is:

1. A balloon catheter, comprising:
an elongate catheter shaft having a proximal section, a distal section, and an inflation lumen defined therein; and
a multilayer balloon on the distal section of the shaft comprising: a first layer made of a first polymer material having a first Shore durometer hardness;
a second layer made of a second polymer material having a second Shore durometer hardness greater than the first Shore durometer hardness, wherein the second layer is an inner layer relative to the first layer; and
a third layer made of a third polymer material having a third Shore durometer hardness less than the second Shore durometer hardness and greater than the first shore hardness, wherein the third layer is an inner layer relative to the second layer.

2. The balloon catheter of claim 1, wherein the multilayer balloon, as blown, has a nominal working diameter.

3. The balloon catheter of claim 2, wherein the balloon has a noncompliant limited radial expansion beyond the nominal working diameter at pressures above a nominal pressure.

4. The balloon catheter of claim 1, wherein the multilayer balloon, as blown, has a compliance less than about 0.035 mm/atm between a nominal pressure and a rated burst pressure.

5. The balloon catheter of claim 2, wherein the balloon has a semicomplaint radial expansion beyond the nominal working diameter at pressures above a nominal pressure.

6. The balloon catheter of claim 1, wherein the multilayer balloon, as blown, has a balloon wall thickness less than 0.003 inch.

7. The balloon catheter of claim 1, wherein the multilayer balloon, as blown, has a balloon wall thickness less than 0.002 inch.

8. The balloon catheter of claim 1, wherein the multilayer balloon, as blown, has a balloon wall thickness less than 0.001 inch.

9. The balloon catheter of claim 1, wherein the multilayer balloon, as blown, has a rated burst pressure is about 15 to about 30 atm.

10. The balloon catheter of claim 2, wherein at least the third layer is substantially at a third layer maximum blow-up-ratio when the multilayer balloon is substantially at the nominal working diameter.

11. The balloon catheter of claim 2, wherein at least the third layer is at a blow up ratio of at least about 90% of a third layer maximum blow-up-ratio when the multilayer balloon is substantially at the nominal working diameter.

12. The balloon catheter of claim 2, wherein at least the third layer is at a blow up ratio of at least about 80% of a third layer maximum blow-up-ratio when the multilayer balloon is substantially at the nominal working diameter.

13. The balloon catheter of claim 1, wherein the third layer has a blow-up-ratio between about 7.0 and about 8.0.

14. The balloon catheter of claim 1, wherein the third layer has a blow-up-ratio between about 7.2 and about 7.8.

15. The balloon catheter of claim 2, wherein the second layer is at a blow up ratio of at least 80% of a second layer maximum blow-up-ratio when the multilayer balloon is substantially at the nominal working diameter.

16. The balloon catheter of claim 2, wherein the second layer is at a blow up ratio of at least 70% of a second layer maximum blow-up-ratio when the multilayer balloon is substantially at the nominal working diameter.

17. The balloon catheter of claim 2, wherein the first layer is at a blow up ratio at least 60% of a first layer maximum blow-up-ratio when the multilayer balloon is substantially at the nominal working diameter.

18. The balloon catheter of claim 1, further comprising an expandable stent mounted on an outer surface of the multilayer balloon.

19. The balloon catheter of claim 1, wherein the first Shore durometer hardness is about 70D.

20. The balloon catheter of claim 1, wherein the second Shore durometer hardness is about 72D or greater.

21. The balloon catheter of claim 1, wherein the third Shore durometer hardness is less than about 70D.

22. The balloon catheter of claim 2, wherein the first Shore durometer hardness is about 70D, the second Shore durometer hardness is about 72D, and the third Shore durometer hardness is about 63D.

23. The balloon catheter of claim 22, wherein the first polymer material is a polyether block amide, the second polymer material is a polyether block amide, and the third polymer material is a polyether block amide.

24. The balloon catheter of claim 23, wherein the balloon has a semicomplaint radial expansion beyond the nominal working diameter at pressures above a nominal pressure.

25. The balloon catheter of claim 2, wherein the first Shore durometer hardness is about 70D, the second Shore durometer hardness is about 74D or greater, and the third Shore durometer hardness is about 63D.

26. The balloon catheter of claim 25, wherein the first polymer material is a polyether block amide, the second polymer material is a nylon, and the third polymer material is a polyether block amide.

27. The balloon catheter of claim 26, wherein the balloon has a noncompliant limited radial expansion beyond the nominal working diameter at pressures above a nominal pressure.

28. The balloon catheter of claim 1, wherein the first Shore durometer hardness is between about 70D and about 72D, the second Shore durometer hardness is about 74D or greater, and the third Shore durometer hardness is between about 63D and about 70D.

29. The balloon catheter of claim 1, wherein the third layer defines an inner surface of the balloon.

30. The balloon catheter of claim 29, wherein the first layer defines an outer surface of the balloon.

31. The balloon catheter of claim 1, wherein the first layer, the second layer, and the third layer are coextruded.

32. A method of making a balloon catheter comprising: providing a tube having at least a first layer, a second layer, and a third layer, wherein the first layer is made of a first polymer material having a first Shore durometer hardness; the second layer is made of a second polymer material having a second Shore durometer hardness greater than the first Shore durometer hardness, wherein the second layer is an inner layer relative to the first layer; and the third layer is made of a third polymer material having a third Shore durometer hardness less than the second Shore-durometer hardness and greater than the first Shore hardness, wherein the third layer is an inner layer relative to the second layer; radially expanding the tube in a mold to form a balloon having a nominal working diameter; providing an elongate catheter shaft having a proximal section, a distal section, and an inflation lumen defined therein; and disposing the balloon on the distal section of the shaft.

33. The method of claim 32, wherein the tube is formed by coextruding the first layer, the second layer, and the third layer.

34. The method of claim 32, wherein the tube is radially expanded in the mold via a single blow process.

35. The method of claim 32, wherein the tube is radially expanded in the mold via a double blow process.

* * * * *